United States Patent
Laba et al.

(10) Patent No.: US 6,210,709 B1
(45) Date of Patent: Apr. 3, 2001

(54) FLEXIBLE GELATIN FREE ENCAPSULATION MATERIAL USEFUL FOR PHARMACEUTICALS, PAINT BALLS AND OTHER FORMULATIONS

(75) Inventors: Dennis Laba, Langhorne; James Gambino, Yardley, both of PA (US)

(73) Assignee: Elementis Specialties, Inc., Hightstown, NJ (US)

( * ) Notice: Subject to any disclaimer, the term of this patent is extended or adjusted under 35 U.S.C. 154(b) by 0 days.

(21) Appl. No.: 09/275,090

(22) Filed: Mar. 24, 1999

(51) Int. Cl.$^7$ ....................................................... A61K 9/48
(52) U.S. Cl. ........................ 424/451; 424/401; 424/455; 424/452; 514/772.2; 514/778; 514/772.3
(58) Field of Search ................................... 424/451, 452, 424/455, 401

(56) References Cited

U.S. PATENT DOCUMENTS

| | | | | |
|---|---|---|---|---|
| 4,738,724 | * | 4/1988 | Wittwer et al. | 106/213 |
| 5,353,712 | * | 10/1994 | Olson | 102/513 |
| 5,393,054 | * | 2/1995 | Rouffer | 273/58 |

* cited by examiner

*Primary Examiner*—James M. Spear
(74) *Attorney, Agent, or Firm*—Michael J. Cronin

(57) ABSTRACT

A flexible capsule formed from a modified starch free of animal based gelatin. The invention provides a novel capsule defining a closed interior chamber, the capsule being formulated from a composition which is free of animal based gelatin comprising at least one plant based starch having been modified to have gelatin like properties; and a paint ball formulation, drug, vitamin, perfume or bath product contained within the capsule.

21 Claims, No Drawings

FLEXIBLE GELATIN FREE ENCAPSULATION MATERIAL USEFUL FOR PHARMACEUTICALS, PAINT BALLS AND OTHER FORMULATIONS

FIELD OF THE INVENTION

The invention relates to a flexible capsule which is largely free of animal based gelatin.

BACKGROUND OF THE INVENTION

The use of gelatin capsules as delivery devices is well-known in many art fields, such as paint balls, pharmaceutical gelatin capsules, vitamin/health formulations using capsules, perfume/cosmetic/bath and gel encapsulated products. Such capsules are flexible and easily dissolved.

All conventional and present day commercial capsules use animal-based gelatin to provide the needed combination of flexibility and strength. However, the use of animal based gelatin has become undesirable in certain cases from the viewpoint of the transmission of diseases, such as the now well known "mad cow" disease in Europe. Furthermore, there is an increasing demand for encapsulation products free of any animal-based components to serve increasing market segments who make judgments based on health considerations as well as other factors.

There are a number of prior art patents that describe capsule formulations. U.S. Pat. No. 5,434,069 discloses a capsule for protecting sensitive ingredients in detergent compositions. The shell is formed from a water soluble polymer selected from polyvinyl alcohol, polyacrylamide, polyvinyl pyrrolidone, carrageenan, guar gum, xantham gum, cellulose or protein.

U.S. Pat. No. 5,641,512 discloses a soft edible gelatin capsule formed from gelatin, plasticizer and a xanthine derivative.

U.S. Pat. No. 3,989,852 discloses a method for encapsulation which utilizes cellulose. Gelatin is listed as a suitable filler. This patent teaches that starch and water should not be used because they form a brittle and flaky layer upon drying. U.S. Pat. No. 4,935,243 discloses chewable, edible soft gelatin capsule which contains gelatin and hydrogenated starch hydrolysate. U.S. Pat. No. 5,817,323 discloses a soft edible gelatin capsule which is formed from gelatin, plasticizer and a starch.

SUMMARY OF THE INVENTION

An objective of the invention is to provide a flexible capsule free of animal based gelatin. The above objective and other objectives are surprisingly obtained by using a plant based starch which has been modified to possess gelatin like properties.

The invention provides a novel encapsulated material comprising:

a capsule defining a closed interior chamber, the capsule being formulated from a composition which is free of animal based gelatin comprising at least one plant based starch having been modified to have gelatin like properties; and a material contained within the capsule.

The invention also provides a novel paint ball comprising:

a capsule defining a closed interior chamber, the capsule being formulated from a composition which is free of animal based gelatin comprising at least one plant based starch having been modified to have gelatin like properties; and a paint material contained within the capsule.

DETAILED DESCRIPTION OF PREFERRED EMBODIMENTS

The flexible capsules according to the present invention are free of animal based gelatin. In place of the gelatin, a starch is utilized which has been modified to have gelatin like properties. The flexible capsules include, for example, paint balls, pharmaceutical gelatin capsules, vitamin/health formulations using capsules, perfume/cosmetic/bath and gel encapsulated products.

Starch is a carbohydrate polymer having the following repeating unit:

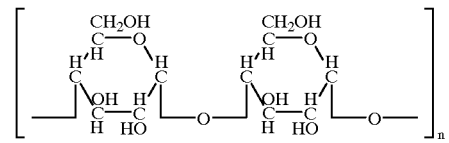

Starches vary largely in the number of the repeating unit (n) in the polymer, which to a major extent depends on the source of the starch. Starch is normally composed of about 25% amylose and 75% amylopectin. Amylose is currently considered by scientists as a mixture of linear and slightly branched molecules whereas amylopectin is considered a densely branched, high molecular weight molecule. In some cereal starches, the amylose content can be as low as 0–1% as in waxy barley, waxy sorghum, and waxy corn and can be as high was 50–70% in some corn hybrids. Starch is often described as a repeating polymer of glucose units linked together by glycosidic bonds.

Starch is a polysaccharide obtained from plants, of which wheat, corn, potato, tapioca and rice are common commercial sources. Without the various modifications discussed herein, starch is a white, semi-crystalline, tasteless powder often in granule form. When starch is mixed with hot water in sufficient amount, such as at a temperature of 65° C. or higher, irreversible gelatinization can occur. Swelling of starch granules can be induced at lower temperatures by the addition of such compounds as formamide, formic acid, and strong bases and certain metallic salts. A large number of pure starch grades are available including those commonly referred to as commercial, powdered, pearl, laundry, technical and edible. Preferably, edible starches are modified and used to form the flexible capsule.

The starch must be modified to have gelatin like properties. Gelatin like properties include the combination of flexibility and strength when formed into a capsule or film. Based on the disclosure provided herein, one skilled in the art will easily be able to formulate and select modified starches which are suitable for forming flexible capsules according to the present invention. As shown in the Examples, by using animal based gelatin as a control, those modified starches which provide a film having at least 80% of both flexibility and strength of the control gelatin film are suitable (index of at least 4). Preferably, a modified starch is selected which provides a film having at least 90% of both flexibility and strength of the control gelatin film. Combinations of modified starches with film strengtheners such as polyvinyl alcohol can be used to provide the required combination of flexibility and strength.

Examples of suitable modifications for modifying the strength and flexibility characteristics of starches include cross-linking, substituting functional groups on the polymer chain, oxidizing, and acid-thinning. Preferably, the starch is modified by well known oxidizing techniques. The Code of Federal Regulations, which is incorporated herein by reference, describes in detail starches and modified starches intended for industrial or food applications. For example, 21 CFR 172.892 describes modification of starch for food use and 21 CFR 178.3520 covers the modification of starch for industrial applications. Starch-based polymers are reaction polyols derived from a reaction, using catalysts, of a starch with dibasic acids and hydrogen-donating compounds dissolved in a water slurry; the slurry is subjected to high temperatures and pressures, yielding a low-viscosity polymer in an aqueous solution. Molecular rearrangement takes place, and the starch-derived polymer formed can be very different from natural starch in structure. The polymer can be further reacted with acids, bases, and cross-linking agents.

A preferred modified starch is derived from wheat produced by Rheox Inc. bearing the commercial designation EA-2865. EA-2865 is an instant or pregelatinized starch obtained by physical modification of wheat starch.

The modified starch should be present in an amount of from about 20 to about 80% by weight, preferably about 20 to about 50% by weight, based on the total weight of the capsule formulation.

In a preferred embodiment, the flexible capsules of this invention also contain a plasticizer and water.

Any conventional plasticizer can be utilized. Examples of suitable plasticisers include glycerin, xylitol, sorbitol, polyglycyerol, non-crystallizing solutions of sorbitol, glucose, fructose and glucose syrups with varying equivalents. A commercial plasticizer is ANIDRISORB, which is a proprietary mixture of sorbitol, sorbitans, maltitol and mannitol. Most preferably, the plasticizer is glycerin.

The plasticizer should be present in an amount of from about 5 to about 50% by weight, preferably about 10 to about 40% by weight, based on the total weight of the capsule formulation.

Water should be present in an amount of from about 10 to about 70% by weight, preferably about 20 to about 60% by weight, based on the total weight of the capsule formulation.

The capsule formulation can also contain conventional additives for use in capsules, such as colorants, flavors, aromas, and polymers. If desired, unmodified starch can be utilized in combination with the modified starch.

The capsule of this invention can be produced by a variety of known encapsulation processes. For example, the capsule can be prepared according to the coacervation process in which material to be encapsulated is dispersed in the aqueous capsule forming solution. In this procedure, a non-solvent for the modified starch and an electrolyte is added or a pH change or a pressure change is effected to make the capsule. Examples of this coacervation process are described in U.S. Pat. Nos. 4,777,089, 3,943,063 and 4,978,483, all three of which are incorporated herein by reference.

The capsule of the invention also can be prepared by extrusion nozzles as taught in U.S. Pat. Nos. 3,310,612, 3,389,194 or 2,799,897 and GB 1,390,503. In these processes, the material to be encapsulated is extruded through the inert orifice of the nozzle. Simultaneously, the capsule forming solution is extruded through the outer orifice of the nozzle to form a uniform coating on the surface of the material to be encapsulated. The capsule is then formed by breaking the coextrudate at the end of the nozzle orifice by air, centrifuge force, blade or carry fluid to form droplets which are hardened in a nonsolvent of the capsule forming material.

U.S. Pat. No. 5,001,880, incorporated herein by reference, teaches a method for forming paint balls in which the capsule is formed as two parts and then molded together.

The above described processes are not intended to be limiting.

The capsule can be used in place of known gelatin based capsules. For example, when forming paint balls, the capsule according to the present invention can be used in place of the gelatin capsule disclosed in U.S. Pat. No. 5,393,054, which is incorporated herein by reference. When paint balls are formed, the encapsulated paint material preferably comprises about 1 to about 65% polyethylene glycol, about 25 to 45% starch, dye and water.

Food grade modified starch can be utilized such that the capsule is suitable for use in pharmaceutical and vitamin applications. The formation of pharmaceuticals and vitamins is well known in the art and one skilled in the art will be able to utilize the gelatin free formulations described herein in for pharmaceutical and vitamin applications.

The invention will now be further explained with reference to the following non-limiting examples.

EXAMPLES

Examples were formed by combining 35% water, 20% glycerin, and 45% of the test component shown in Table 1 and heating the mixture at 60° C. for 30 minutes. Films were formed by pouring the mixture onto a glass plate angled at about 45° C. The film was allowed to cool, then peeled from the glass. The gelatin control provided a tough, flexible film that dried quickly. The films were tested for strength and flexibility by comparing them to the gelatin control using the index 5 is good and 1 is bad. For example, an index of 4 represents about 80% of the strength or flexibility of the gelatin based film. The test results are shown in Table 1.

TABLE 1

| Component | Strength of Film | Flexibility of Film |
| --- | --- | --- |
| Gelatin Control | 5 | 5 |
| Pregelatinized, Oxidized Wheat Starch | 4 | 4 |
| Modified Wheat Starches | 1–2 | 1–2 |
| Pregelatinized Wheat Starch | 3 | 1–2 |
| Acid Thinned Wheat | 1 | 1 |

TABLE 1-continued

| Component | Strength of Film | Flexibility of Film |
|---|---|---|
| Starch | | |
| Polyvinyl Alcohol | 5 | 2 |

Some modified pregelatinized wheat starches did provide a gel, but not with the combination of strength and flexibility required to form a suitable capsule. When peeled from the glass, they were easily broken. The acid thinned wheat starch was very runny and did not dry to a gel consistency. A known film former, polyvinyl alcohol, provided a film that exhibited good strength, but very poor flexibility. The pregelatinized, oxidized wheat starch, produced by Rheox under the product name EA-2865, provided a combination of strength and flexibility required to form a suitable capsule.

Based on the above, it is believed that a combination of pregelatinized, oxidized wheat starch and polyvinyl alcohol will also provide a suitable encapsulating material where flexibility and strength are required.

It also can be concluded that combining a starch having a good flexibility with a starch having a good strength to make an encapsulation material will result in a combination having both good flexibility and strength.

While the claimed invention has been described in detail and with reference to specific embodiments thereof, it will be apparent to one of ordinary skill in the art that various changes and modifications can be made to the claimed invention without departing from the spirit and scope thereof.

What we claim:

1. An encapsulated material comprising:
   a capsule defining a closed interior chamber, said capsule being formulated from a composition which is free of animal based gelatin comprising at least one plant based starch having been modified to have flexability and strength similar to gelatin wherein said modified starch comprises a pregelantized, oxidized wheat starch; and
   a material contained within said capsule.

2. An encapsulated material according to claim 1, wherein said modified starch being present in an amount of about 20 to about 80%, water being present in an amount of from about 10 to about 70%, and a plasticizer being present in an amount of about 5 to about 60%.

3. An encapsulated material according to claim 1, wherein said modified starch being present in an amount of about 20 to about 50%, water being present in an amount of from about 20 to about 60%, and a plasticizer being present in an amount of about 10 to about 40%.

4. An encapsulated material according to claim 1, wherein said modified starch has been selected to provide a film having at least 80% of the strength and flexibility compared to a gelatin control film.

5. An encapsulated material according to claim 1, wherein said modified starch has been selected to provide a film having at least 90% of the strength and flexibility compared to a gelatin control film.

6. An encapsulated material according to claim 1, which comprises a second starch.

7. An encapsulated material according to claim 6, wherein the material further includes polyvinyl alcohol.

8. An encapsulated material according to claim 2, wherein said plasticizer comprises glycerin.

9. An encapsulated material according to claim 1, wherein said material comprises paint.

10. An encapsulated material according to claim 1, wherein said material comprises a pharmaceutical drug.

11. An encapsulated material according to claim 1, wherein said material comprises a vitamin.

12. An encapsulated material according to claim 1, wherein said material comprises a perfume.

13. An encapsulated material according to claim 1, wherein said material comprises a bath gel.

14. A paint ball comprising:
    a capsule defining a closed interior chamber, said capsule being formulated from a composition which is substantially free of animal based gelatin comprising at least one pregelatinized, oxidized wheat starch having been modified to have flexability and strength similar to gelatin; and
    a paint material contained within said capsule.

15. A paint ball according to claim 14, wherein said paint material comprises about 1 to about 65% polyethylene glycol, about 25 to 45% starch, dye and water.

16. A paint ball according to claim 14, wherein said modified starch being present in an amount of about 20 to about 80%, and also containing water being present in an amount of from about 10 to about 70%, and which also contains a plasticizer being present in an amount of about 5 to about 60%.

17. A paint ball according to claim 16, wherein said modified starch being present in an amount of about 20 to about 50%, said water being present in an amount of from about 20 to about 60%, and a plasticizer being present in an amount of about 10 to about 40%.

18. A paint ball according to claim 14, wherein said modified starch has been selected to provide a film having at least 80% of the strength and flexibility compared to a gelatin control film.

19. A paint ball according to claim 14, wherein said modified starch has been selected to provide a film having at least 90% of the strength and flexibility compared to a gelatin control film.

20. A paint ball according to claim 14, wherein said modified starch comprises a pregelatinized, oxidized wheat starch and polyvinyl alcohol.

21. A paint ball according to claim 16, wherein said plasticizer comprises glycerin.

* * * * *